United States Patent
Tong et al.

(10) Patent No.: US 10,172,783 B2
(45) Date of Patent: Jan. 8, 2019

(54) HIGH UV PROTECTION ALCOHOL-FREE ANHYDROUS CLEAR SYSTEM

(71) Applicant: L'OREAL, Paris (FR)

(72) Inventors: Jun Hua Tong, Jersey City, NJ (US); Paula Cziryak, Eatontown, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/295,744

(22) Filed: Jun. 4, 2014

(65) Prior Publication Data

US 2015/0352035 A1   Dec. 10, 2015

(51) Int. Cl.
| | |
|---|---|
| A61K 8/31 | (2006.01) |
| A61K 8/33 | (2006.01) |
| A61K 8/37 | (2006.01) |
| A61K 8/49 | (2006.01) |
| A61K 8/58 | (2006.01) |
| A61K 8/96 | (2006.01) |
| A61K 8/368 | (2006.01) |
| A61K 8/891 | (2006.01) |
| A61Q 17/04 | (2006.01) |

(52) U.S. Cl.
CPC ............... *A61K 8/96* (2013.01); *A61K 8/31* (2013.01); *A61K 8/33* (2013.01); *A61K 8/368* (2013.01); *A61K 8/37* (2013.01); *A61K 8/498* (2013.01); *A61K 8/4973* (2013.01); *A61K 8/585* (2013.01); *A61K 8/891* (2013.01); *A61Q 17/04* (2013.01); *A61K 2800/262* (2013.01); *A61K 2800/30* (2013.01); *A61K 2800/42* (2013.01)

(58) Field of Classification Search
None
See application file for complete search history.

(56) References Cited

U.S. PATENT DOCUMENTS

| | | | |
|---|---|---|---|
| 2,463,264 | A | 3/1949 | Graenacher et al. |
| 4,077,441 | A | 3/1978 | Rosen et al. |
| 4,264,581 | A * | 4/1981 | Kerkhof ............. A61K 8/35 424/59 |
| 4,850,517 | A | 7/1989 | Ter Stege |
| 5,166,355 | A | 11/1992 | Leistner et al. |
| 5,237,071 | A | 8/1993 | Leistner et al. |
| 5,585,091 | A | 12/1996 | Pelzer et al. |
| 5,624,663 | A | 4/1997 | Deflandre et al. |
| 5,833,961 | A * | 11/1998 | Siegfried ............. A61K 8/35 424/400 |
| 6,093,385 | A | 7/2000 | Habeck et al. |
| 6,159,455 | A | 12/2000 | Habeck et al. |
| 6,225,467 | B1 | 5/2001 | Esteghamatian et al. |
| 6,387,355 | B2 | 5/2002 | Heidenfelder et al. |
| 6,391,289 | B2 | 5/2002 | Heidenfelder et al. |
| 6,436,373 | B1 | 8/2002 | Habeck et al. |
| 2003/0059383 | A1 * | 3/2003 | SaNogueira ......... A61K 8/27 424/59 |
| 2004/0042980 | A1 * | 3/2004 | Kanji ................. A61K 8/88 424/59 |
| 2005/0013782 | A1 | 1/2005 | Goppel et al. |
| 2008/0206172 | A1 | 8/2008 | Mohammadi et al. |
| 2010/0254923 | A1 * | 10/2010 | Galdi ................. A61K 8/37 424/60 |

FOREIGN PATENT DOCUMENTS

| | | |
|---|---|---|
| DE | 19726184 A1 | 12/1998 |
| DE | 19746654 A1 | 2/1999 |
| DE | 19755649 A1 | 6/1999 |
| DE | 19855649 A1 | 6/2000 |
| DE | 10162844 A1 | 7/2003 |
| EP | 0669323 A1 | 8/1995 |
| EP | 0832642 A2 | 4/1998 |
| EP | 0893119 A1 | 1/1999 |
| EP | 0967200 A1 | 12/1999 |
| EP | 1008586 A1 | 6/2000 |
| EP | 1027883 A2 | 8/2000 |
| EP | 1133980 A2 | 9/2001 |
| EP | 1133981 A2 | 9/2001 |
| EP | 1300137 A2 | 4/2003 |
| GB | 2303549 A | 2/1997 |
| WO | 93/04665 A1 | 3/1993 |
| WO | 2004/006878 A1 | 1/2004 |
| WO | 2004/085412 A2 | 10/2004 |
| WO | 2005/058269 A1 | 6/2005 |
| WO | 2006/032741 A1 | 3/2006 |
| WO | 2006/034982 A1 | 4/2006 |
| WO | 2006/034985 A1 | 4/2006 |

(Continued)

OTHER PUBLICATIONS

Sigma-Aldrich "Isopropyl myristate" accessed online on Sep. 27, 2015 at http://www.sigmaaaldrich.com/catalog/product/aldrich/172472?lang=en&region=US.*
Sigma-Aldrich "Isopropyl myristate" accessed online on Sep. 27, 2015 at http://www.sigmaaaldrich.eom/catalog/product/aldrich/172472?lang=&region=US.*
AIC Specification Sheet for "Caprylic/capric triglyceride" accessed online on Sep. 28, 2015 at http ://www.aicma.com/products/Caprylic%20Capric%20Triglyceride%20(waglinol%203-9280)%20CTGLSL.pdf.*

(Continued)

*Primary Examiner* — Carlos A Azpuru
*Assistant Examiner* — Casey S Hagopian
(74) *Attorney, Agent, or Firm* — McNees Wallace & Nurick LLC

(57) ABSTRACT

The present invention is directed to a composition containing: an emollient system containing esters chosen from dicaprylyl ether, isopropyl myristate, caprylic/capric triglyceride, and sorbitan trioleate; sunscreen actives; an oil-soluble film-former; and optionally, an aesthetic modifier, wherein the composition is clear in appearance both during and after its application onto a keratinous substrate, and alcohol-free.

14 Claims, No Drawings

(56) References Cited

FOREIGN PATENT DOCUMENTS

| WO | 2006/034991 A1 | 4/2006 | |
|---|---|---|---|
| WO | 2006/034992 A1 | 4/2006 | |
| WO | 2006/035000 A1 | 4/2006 | |
| WO | 2006/035007 A1 | 4/2006 | |
| WO | 2007/103654 A1 | 9/2007 | |
| WO | WO 2013060559 A1 * | 5/2013 | ............ A61K 8/375 |

OTHER PUBLICATIONS

Author anonymous; Symmetrical Triazine Derivatives; 127 pages; Published on Sep. 20, 2004; IP.com Prior Art Database Disclosure; Ref. IPCOM000031257D; IP.com, 100 Willowbrook Office Park, Suite 100, Fairport, NY 14450.

* cited by examiner

HIGH UV PROTECTION ALCOHOL-FREE ANHYDROUS CLEAR SYSTEM

BACKGROUND OF THE INVENTION

Conventional sunscreen products generally take the form of ultraviolet (UV)-filter compounds and/or particulate UV-screening compounds (collectively, "sunscreen actives") that are solubilized, emulsified, or dispersed in a vehicle, which is topically applied to the skin. The sunscreen actives, typically through the aid of polymers and other ingredients included in the vehicle, form a thin, protective, and often water-resistant layer on the skin.

Most organic sunscreen agents are oil-like and/or oil-soluble materials. High levels of these actives in sun care products render the products less appealing for their greasy skin feel and skin irritation.

Anhydrous sunscreen products are desired by consumers because of their easy and pleasant application to the skin and their good water resistance. Monohydric $C_1$-$C_3$ alcohols are typically used in anhydrous products, as they are inherently clear, and their volatility results in a dry feel. In addition, the use of monohydric alcohols helps prevent phase separation over time. Currently marketed clear sunscreen sprays may contain greater than 40% alcohols.

However, there are disadvantages to the use of monohydric $C_1$-$C_3$ alcohols in formulations. Products containing alcohols require special safety measures be taken during production, storage, and transportation. In addition, alcohol-containing products are potentially flammable during use. In products containing film formers, alcohols may effectively adhere to the skin and may ignite when in contact with a flame. Alcohol-free products are of interest to consumers because of odor, tolerance, and safety.

Among sunscreen products, sprays are gaining increasing consumer preference because of their convenience and ease of application. However, traditional sunscreen sprays suffer from greasy feel and white and/or shiny residue left on the skin after application.

The applicants have recognized that severe aesthetic and performance problems still exist in most all sunscreen spray products. Accordingly, the applicants have now identified an alcohol-free sunscreen composition that has a light, dry feel, low shine, and is clear when applied onto the skin.

BRIEF SUMMARY OF THE INVENTION

The present invention is directed to a composition comprising:
(a) an emollient system containing esters chosen from dicaprylyl ether, isopropyl myristate, caprylic/capric triglyceride, and sorbitan trioleate;
(b) sunscreen actives;
(c) an oil-soluble film-former; and
(d) optionally, an aesthetic modifier;
wherein the composition is clear in appearance when applied onto skin and alcohol-free.

The present invention is also directed to a process of protecting a keratinous substrate from harmful effects of UV radiation by instructing users to apply the above-disclosed composition onto a keratinous substrate.

The present invention is also directed to a method of making the above-disclosed composition by combining ingredients (a)-(d).

DETAILED DESCRIPTION OF THE INVENTION

The inventors have surprisingly discovered an alcohol-free, anhydrous composition, comprising a certain emollient system, sunscreen actives, and an oil-soluble film-former yields a composition which, when applied onto a keratinous substrate such as skin, hair or nails, has a dry feel and quick absorption without oiliness while remaining clear in appearance both during and after application onto the keratinous substrate.

Other than in the operating examples, or where otherwise indicated, all numbers expressing quantities of ingredients and/or reaction conditions are to be understood as being modified in all instances by the term "about".

As used herein, the expression "at least one" means one or more and thus includes individual components as well as mixtures/combinations.

"Cosmetically acceptable" means that the item in question is compatible with any keratinous substrate. For example, "cosmetically acceptable carrier" means a carrier that is compatible with any keratinous substrate.

A "physiologically acceptable medium" means a medium which is not toxic and can be applied to the skin, lips, hair, scalp, lashes, brows, nails or any other cutaneous region of the body. The composition of the instant disclosure may especially constitute a cosmetic or dermatological composition.

The term "alcohol-free" as used herein means containing less than 5%, such as less than 3%, such as less than 1% by weight, based on the total active weight of the composition, of $C_1$-$C_3$ monohydric alcohols such as methanol, ethanol, and propanol.

The term "anhydrous" as used herein means containing less than 5%, such as less than 3%, such as less than 1% by weight, based on the total active weight of the composition, of water.

The term "clear" as used herein means that after applying a film of the composition onto a glass plate, and then placing the glass plate over top of a printed document, a person is able to read 12 point font through the film+plate with their naked eye.

Emollients

The present invention comprises an emollient mixture which yields a composition having a light, dry feel, low shine, and that is clear prior to and after application onto a keratinous substrate. Emollients having flash points greater than 100° C. were chosen based on their molecular weight, density, and refractive index. Emollients were chosen to counteract the molecular weight, refractive index, and density of the UV filters. Molecular weight, density, and refractive index of the emollients were optimized to afford a composition having a light, non-greasy feel while at the same time having good performance.

Suitable emollients for use in the present invention are those having a density of from about 0.8 g/ml to about 0.95 g/mol; and a refractive index of from about 1.43 to less than 1.51.

Examples of suitable emollients for use in the present invention include, but are not limited to, fatty acid esters; fatty acid triglycerides; monocarboxylic acid esters; synthetic ethers; sorbitan fatty acid esters; hydrocarbon oils; and mixtures thereof these.

Suitable fatty acid ester emollients include those derived from C12-C50 fatty acids, preferably C16-C22 saturated fatty acids, and monohydric alcohols. Examples of such esters include isopropyl myristate, methyl palmitate, isopropyl laurate, isopropyl palmitate, ethylhexyl palmitate, myristyl myristate, and mixtures thereof.

Suitable fatty acid triglyceride emollients include those which are synthetic or naturally occurring. Fatty acid triglycerides are generally fatty acid triesters of glycerol, the fatty acids of which may have chain lengths from C4 to C24, these chains possibly being linear or branched, and saturated or unsaturated. Examples of such fatty acid triglyceride emollients include wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, safflower oil, and caprylic/capric acid triglycerides.

Suitable monocarboxylic acid ester emollients include those of the general formula R'COOR, wherein R' and R are straight or branched chain, saturated or unsaturated alkyl, aryl, and wherein sum of carbon atoms in R' and R is at least 10. A suitable monoester is alkyl benzoate such as C12-15 alkyl benzoate.

Suitable synthetic ether emollients include those containing from 10 to 40 carbon atoms, such as dicaprylyl ether.

Suitable sorbitan fatty acid ester emollients include sorbitan oleates such as sorbitan trioleate.

The compositions according to the invention may comprise one or more volatile hydrocarbon-based oils. As volatile hydrocarbon-based oils that may be used according to the invention, mention may be made especially of hydrocarbon-based oils containing from 8 to 16 carbon atoms, and especially branched C8-C16 alkanes such as C8-C16 isoalkanes of petroleum origin (also known as isoparaffins), for instance isododecane (also known as 2,2,4,4,6-pentamethylheptane), isodecane, and isohexadecane.

The amount of emollient system present in the composition of the present invention is typically employed in an amount of from about 5% to 95% by weight, more preferably from about 20% to 90% by weight, and most preferably from about 50% to 80% by weight, all weights based on the total active weight of the composition.

Similarly, the weight ratio of emollient system to sunscreen actives is from about 2.0:1 to about 3.2:1, preferably from about 2.3:1 to about 2.9:1, and most preferably from about 2.5:1 to about 2.7:1.

Sunscreen Actives

The organic UV-screening agents are chosen especially from cinnamic derivatives; anthranilates; salicylic derivatives; dibenzoylmethane derivatives; camphor derivatives; benzophenone derivatives; β,β-diphenylacrylate derivatives; triazine derivatives; benzotriazole derivatives; benzalmalonate derivatives, especially those cited in patent U.S. Pat. No. 5,624,663; benzimidazole derivatives; imidazolines; bis-benzoazolyl derivatives as described in patents EP669323 and U.S. Pat. No. 2,463,264; p-aminobenzoic acid (PABA) derivatives; methylene bis(hydroxyphenylbenzotriazole) derivatives as described in applications U.S. Pat. Nos. 5,237,071, 5,166,355, GB2303549, DE19726184 and EP893119; benzoxazole derivatives as described in patent applications EP0832642, EP1027883, EP1300137 and DE10162844; screening polymers and screening silicones such as those described especially in patent application WO 93/04665; dimers derived from α-alkylstyrene such as those described in patent application DE19855649; 4,4-diarylbutadienes such as those described in patent applications EP0967200, DE19746654, DE19755649, EP-A-1008586, EP1133980 and EP1133981, merocyanine derivatives such as those described in patent applications WO 04/006878, WO 05/058269 and WO 06/032741; and mixtures thereof.

As examples of complementary organic photoprotective agents, mention may be made of those denoted hereinbelow under their INCI name:

Cinnamic Derivatives:
Ethylhexyl Methoxycinnamate sold in particular under the trade name "Parsol® MCX" by DSM Nutritional Products, Isopropyl Methoxycinnamate, Isoamyl Methoxycinnamate sold under the trade name "Neo Heliopan® E 1000" by Symrise, DEA Methoxycinnamate, Diisopropyl Methylcinnamate, Glyceryl Ethylhexanoate Dimethoxycinnamate.

Dibenzoylmethane Derivatives:
Butyl Methoxydibenzoylmethane sold especially under the trade name "Parsol® 1789" by DSM, Isopropyl Dibenzoylmethane.

Para-Aminobenzoic Acid Derivatives:
PABA, Ethyl PABA, Ethyl Dihydroxypropyl PABA, Ethylhexyl dimethyl PABA sold in particular under the name "Escalol™ 507" by ISP, Glyceryl PABA, PEG-25 PABA sold under the name "Uvinul® P25" by BASF.

Salicylic Derivatives:
Homosalate sold under the name "Eusolex® HMS" by Rona/EM Industries, Ethylhexyl Salicylate sold under the name "Neo Heliopan® OS" by Symrise, Dipropylene Glycol Salicylate sold under the name "Dipsal™" by Scher, TEA Salicylate sold under the name "Neo Heliopan® TS" by Symrise.

β,β-Diphenylacrylate Derivatives:
Octocrylene sold in particular under the trade name "Uvinul® N539" by BASF, Etocrylene sold in particular under the trade name "Uvinul® N35" by BASF.

Benzophenone Derivatives:
Benzophenone-1 sold under the trade name "Uvinul® 400" by BASF, Benzophenone-2 sold under the trade name "Uvinul® D50" by BASF, Benzophenone-3 or Oxybenzone sold under the trade name "Uvinul® M40" by BASF, Benzophenone-4 sold under the trade name "Uvinul® MS40" by BASF, Benzophenone-5, Benzophenone-6 sold under the trade name "Helisorb® 11" by Norquay, Benzophenone-8 sold under the trade name "Spectra-Sorb UV-24" by American Cyanamid, Benzophenone-9 sold under the trade name "Uvinul® DS-49" by BASF, Benzophenone-12, n-Hexyl 2-(4-diethylamino-2-hydroxybenzoyl)benzoate sold under the trade name "Uvinul® A+" or as a mixture with octyl methoxycinnamate under the trade name "Uvinul® A+B" by BASF.

Benzylidenecamphor Derivatives:
3-Benzylidene Camphor manufactured under the name "Mexoryl™ SD" by Chimex, 4-Methylbenzylidene Camphor sold under the name "Eusolex® 6300" by Merck, Benzylidene Camphor Sulfonic Acid manufactured under the name "Mexoryl™ SL" by Chimex, Camphor Benzalkonium Methosulfate manufactured under the name "Mexoryl™ SO" by Chimex, Terephthalylidene Dicamphor Sulfonic Acid manufactured under the name "Mexoryl™ SX" by Chimex, Polyacrylamidomethyl Benzylidene Camphor manufactured under the name "Mexoryl™ SW" by Chimex.

Phenylbenzimidazole Derivatives:
Phenylbenzimidazole Sulfonic Acid sold in particular under the trade name "Eusolex® 232" by Merck, Disodium Phenyl Dibenzimidazole Tetrasulfonate sold under the trade name "Neo Heliopan® AP" by Symrise.

Phenylbenzotriazole Derivatives:
Drometrizole Trisiloxane sold under the name "Silatrizole" by Rhodia Chimie, Methylene bis-Benzotriazolyl Tetramethylbutyl-phenol sold in solid form under the trade name "MIXXIM BB/100" by Fairmount Chemical, or in micronized form as an aqueous dispersion under the trade name "Tinosorb M" by Ciba Specialty Chemicals.

Triazine Derivatives:

bis-Ethylhexyloxyphenol Methoxyphenyl Triazine sold under the trade name "Tinosorb® S" by BASF, Ethylhexyl Triazone sold in particular under the trade name "Uvinul® T150" by BASF, Diethylhexyl Butamido Triazone sold under the trade name "Uvasorb® HEB" by Sigma 3V, 2,4,6-tris(dineopentyl 4'-aminobenzalmalonate)s-triazine, 2,4,6-tris(diisobutyl 4'-aminobenzalmalonate)-s-triazine, 2,4-bis(dineopentyl 4'-aminobenzalmalonate)-6-(n-butyl 4'-aminobenzoate)-s-triazine, symmetrical triazine screening agents described in patent U.S. Pat. No. 6,225,467, patent application WO 2004/085412 (see compounds 6 and 9) or the document "Symmetrical Triazine Derivatives" IP.COM Journal, IP.COM Inc., West Henrietta, N.Y., US (20 Sep. 2004), especially 2,4,6-tris(biphenyl)-1,3,5-triazines (in particular 2,4,6-tris(biphenyl-4-yl)-1,3,5-triazine and 2,4,6-tris(terphenyl)-1,3,5-triazine, which is included in patent applications WO 06/035000, WO 06/034982, WO 06/034991, WO 06/035007, WO 2006/034992 and WO 2006/034985).

Anthranilic Derivatives:

Menthyl Anthranilate sold under the trade name "Neo Heliopan® MA" by Symrise.

Imidazoline Derivatives:

Ethylhexyl Dimethoxybenzylidene Dioxoimidazoline Propionate.

Benzalmalonate Derivatives:

Polyorganosiloxane containing benzalmalonate functions, for instance Polysilicone-15, sold under the trade name "Parsol® SLX" by DSM Nutritional Products.

4,4-Diarylbutadiene Derivatives:

1,1-dicarboxy(2,2'-dimethylpropyl)-4,4-diphenylbutadiene.

Benzoxazole Derivatives:

2,4-bis[5-(1-dimethylpropyl)benzoxazol-2-yl-(4-phenyl)imino]-6-(2-ethylhexyl)imino-1,3,5-triazine sold under the name Uvasorb® K2A by Sigma 3V, and mixtures thereof.

The Preferential Organic Screening Agents are Chosen From:

Ethylhexyl Methoxycinnamate, Ethylhexyl Salicylate, Homosalate, Butyl Methoxydibenzoylmethane, Octocrylene, Phenylbenzimidazole Sulfonic Acid, Benzophenone-3, Benzophenone-4, Benzophenone-5, n-Hexyl 2-(4-diethylamino-2-hydroxybenzoyl)benzoate, 4-Methylbenzylidene Camphor, Terephthalylidene Dicamphor Sulfonic Acid, Disodium Phenyl Dibenzimidazole Tetrasulfonate, Methylene Bis-Benzotriazolyl Tetramethylbutylphenol, Bis-Ethylhexyloxyphenol Methoxyphenyl Triazine, Ethylhexyl triazone, Diethylhexyl Butamido Triazone, 2,4,6-Tris(dineopentyl 4'-aminobenzalmalonate)-s-triazine, 2,4,6-Tris(diisobutyl 4'-aminobenzalmalonate)-s-triazine, 2,4-Bis(dineopentyl 4'-aminobenzalmalonate)-6-(n-butyl 4'-aminobenzoate)-s-triazine, 2,4,6-Tris(biphenyl-4-yl)-1,3,5-triazine, 2,4,6-Tris(terphenyl)-1,3,5-triazine, Drometrizole Trisiloxane, Polysilicone-15, 1,1-dicarboxy(2,2'-dimethylpropyl)-4,4-diphenylbutadiene, 2,4-bis[5-1(dimethylpropyl)benzoxazol-2-yl-(4-phenyl)imino]-6-(2-ethylhexyl)imino-1,3,5-triazine, and mixtures thereof.

The sunscreen actives according to the invention are present in the compositions according to the invention in an amount ranging from about 2% to 40% by weight, preferably from about 22% to 36% by weight, and most preferably from about 20% to 30% by weight, based on the total active weight of the composition.

Oil Soluble Film Former

The compositions of the present invention also contain at least one oil soluble film former. Examples of suitable oil soluble film formers include ethylenediamine/stearyl dimer dilinoleate copolymer, vp/hexadecene copolymer, vp/eicosene copolymer, synthetic wax, beeswax, polyethylene, perfluoroperhydrophenanthrene, adipic acid/diethylene glycol/glycerin crosspolymer, trimethylpentanediol/adipic acid/glycerin copolymer, hydrogenated styrene/butadiene coplymer, hydrogenated styrene/isoprene copolymer, hydrogenated polycyclopentadiene, and propylsilsesquioxane wax substituted with alkyl units having at least 30 carbons.

One such polypropylsilsesquioxane wax is a C30-45 alkyldimethylsilyl polypropylsilsesquioxane commercially available from Dow Corning under the tradename SW-8005 C30 Resin Wax. The amount of oil soluble film former present in the composition of the present invention is typically from about 0.75% to 2.75%, more preferably from about 1.0% to 2.0%, and most preferably from about 1.25% to 1.75% by weight, all weights based on the total active weight of the composition.

According to one particular preferred embodiment, in the event polypropylsilsesquioxane wax is employed as the oil-soluble film former, it is oftentimes dissolved in a volatile hydrocarbon-based oil such as paraffin.

Aesthetic Modifier

A composition according to the invention may also comprise at least one aesthetic modifier in order to optimize the stability, the light residue, the matte effect and the non-greasy feeling on the skin.

Examples of suitable aesthetic modifiers include nylon-12, polymethylmethacrylate crosspolymer, silica silylate, methyl methacrylate crosspolymer and polymethylsilsesquioxane.

One type of aesthetic modifier which may be used is hydrophobic aerogel particles whose INCI name is silica silylate sold by Dow Corning under the name VM-2270 Aerogel Fine Particles.

The aesthetic modifier is present in amounts ranging from about 0.1% to 5%, more preferably from about 1.5% to 2.5% and even more preferably from about 0.75% to 1.5% relative to the total weight of the composition.

The compositions according to the invention are employed in the form of vaporizable lotions which can be applied onto a keratinous substrate in the form of fine particles by means of pressurization devices. The devices in accordance with the invention are well known to those skilled in the art and comprise non-aerosol pumps or "atomizers", the aerosol containers comprising a propellant, and also aerosol pumps using compressed air as propellant. These pumps are described in patents U.S. Pat. No. 4,077,441 and U.S. Pat. No. 4,850,517, all of which are incorporated herein by reference.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 70% by weight relative to the total weight of the composition.

The following examples serve to illustrate the invention without however exhibiting a limiting character. In these examples the amounts of the composition ingredients are given as weight percentages relative to the total weight of the composition.

EXAMPLES

TABLE 1

Inventive Examples

| INGREDIENTS | Example 1 | Example 2 |
|---|---|---|
| ISOPROPYL MYRISTATE | 22.45 | 24.10 |
| SORBITAN TRIOLEATE | 2.40 | 2.40 |
| DICAPRYLYL ETHER | 6.00 | 0 |
| MYRISTYL MYRISTATE | 0 | 2.40 |
| C12-15 ALKYL BENZOATE | 4.20 | 3.60 |
| CAPRYLIC/CAPRIC TRIGLYCERIDE | 7.20 | 0 |
| ISOHEXADECANE | 0 | 9.60 |
| C30-45 ALKYLDIMETHYLSILYL POLYPROPYLSILSESQUIOXANE (and) PARAFFIN | 0.90 | 0.90 |
| UV FILTERS | 16.07 | 16.07 |
| SILICA SILYATE | 0.59 | 0.15 |
| TOCOPHEROL | 0.06 | 0.06 |
| POLYMETHYLSILSESQUIOXANE | 0 | 0.60 |
| FRAGRANCE | 0.12 | 0.12 |
| PROPELLANT | 40.00 | 40.00 |

In making each of the examples in Table 1, the following procedure was used. All ingredients except the propellant were combined, heated to 85° C., and mixed until homogeneous. After cooling to room temperature, mixture was dispensed into aerosol cans. The aerosol cans were crimped and propellant was injected into each of the aerosol cans.

Consumer perception and performance of Example 1 was compared against a leading alcohol-based clear continuous spray sunscreen SPF 50 and evaluated in a sequential monadic test. The products were presented in blinded aerosol cans. The products were rotated randomly. Each product was evaluated after one week of use. The panel consisted of 80 participants ranging in age from 18 to 65, having all skin types, and users of a mass market spray SPF 30+ sunscreen on the body when spending time outdoors or in the sun. ANOVA test was preformed, and statistically significant differences on the means were reported at the 95% confidence interval.

TABLE 2

Consumer Perception of Example 1 vs. Leading Alcohol-based Clear Continuous Spray Sunscreen SPF 50 (contains over 50% alcohol)

| | Rating | |
|---|---|---|
| Attribute of Product | Example 1 | Leading Alcohol-based Clear Continuous Spray Sunscreen SPF50 |
| Overall appearance | favorable | favorable |
| Color | favorable | favorable |
| Absorption time | favorable | favorable |
| Greasiness | favorable | favorable |

The conclusions show that composition of Example 1 performs similar to the benchmark. This demonstrates the composition of Example 1 performs on par with an alcohol-containing formula.

What is claimed is:

1. A composition consisting essentially of:
   (a) from about 50% to 80% of an emollient system containing esters chosen from:
      dicaprylyl ether, isopropyl myristate, caprylic/capric triglyceride, myristyl myristate, alkyl benzoate, isohexadecane, alkyldimethylsilyl polypropylsilsesquioxane and paraffin, and sorbitan trioleate,
      wherein the esters of the emollient system have a density of from about 0.8 g/ml to about 0.95 g/mol, and a refractive index of from about 1.43 to less than 1.51;
   (b) one or more sunscreen actives;
   (c) from about 1.25% to 1.75% by weight, based on the total active weight of the composition, of at least one oil-soluble film-former selected from the group consisting of synthetic wax, beeswax, polyethylene, perfluoroperhydrophenanthrene, adipic acid/diethylene glycol/glycerin crosspolymer, trimethylpentanediol/adipic acid/glycerin copolymer, hydrogenated styrene/butadiene coplymer, hydrogenated styrene/isoprene copolymer, hydrogenated polycyclopentadiene, and propylsilsesquioxane wax substituted with alkyl units having at least 30 carbons; and
   (d) from about 0.75% to 1.5% by weight, based on the total active weight of the composition, of at least one aesthetic modifier selected from the group consisting of silica silylate and polymethylsilsesquioxane,
   wherein the composition is clear in appearance both during and after its application onto a targeted keratinous substrate, anhydrous and alcohol free.

2. The composition of claim 1 wherein (a) and (b) are employed in a weight ratio of from about 2.0:1 to about 3.2:1.

3. The composition of claim 2 wherein (a) and (b) are employed in a weight ratio of from about 2.3:1 to about 2.9:1.

4. The composition of claim 1 wherein (b) is employed in an amount of from about 2% to 40% by weight, based on the total active weight of the composition.

5. The composition of claim 1 wherein the composition has an SPF ranging from about 15 to 70.

6. The composition of claim 1, wherein the composition is devoid of silica silylate.

7. The composition of claim 1, wherein the composition is devoid of synthetic wax.

8. The composition of claim 1, wherein the esters are isopropyl myristate or sorbitan trioleate.

9. A method of protecting a keratinous substrate from UV radiation comprising applying the composition of claim 1 onto a targeted keratinous substrate.

10. A composition comprising:
   (a) from about 50% to 80% by weight, based on the total active weight of the composition, of an emollient system;
   (b) one or more sunscreen actives;
   (c) from about 1.25% to 1.75% by weight, based on the total active weight of the composition, of at least one oil-soluble film-former;
   (d) from about 0.75% to 1.5% by weight, based on the total active weight of the composition, of at least one aesthetic modifier; and
   (e) one or more propellants,
   wherein the composition is atomizable and is clear in appearance both during and after its application onto a targeted keratinous substrate, anhydrous and alcohol free.

11. The composition of claim 10, wherein the emollient system contains esters chosen from dicaprylyl ether, isopropyl myristate, caprylic/capric triglyceride, myristyl myristate, alkyl benzoate, isohexadecane, alkyldimethylsilyl polypropylsilsesquioxane and paraffin, and sorbitan trioleate.

12. The composition of claim 11, wherein the esters of the emollient system have a density of from about 0.8 g/ml to about 0.95 g/mol, and a refractive index of from about 1.43 to less than 1.51.

13. The composition of claim 10, wherein the at least one oil-soluble film-former is selected from the group consisting of ethylenediamine/stearyl dimer dilinoleate copolymer, vp/hexadecene copolymer, vp/eicosene copolymer, synthetic wax, beeswax, polyethylene, perfluoroperhydrophenanthrene, adipic acid/diethylene glycol/glycerin crosspolymer, trimethylpentanediol/adipic acid/glycerin copolymer, hydrogenated styrene/butadiene coplymer, hydrogenated styrene/isoprene copolymer, hydrogenated polycyclopentadiene, and propylsilsesquioxane wax substituted with alkyl units having at least 30 carbons.

14. The composition of claim 10, wherein the at least one aesthetic modifier is selected from the group consisting of nylon-12, polymethylmethacrylate crosspolymer, silica silylate, methyl methacrylate crosspolymer, and polymethylsilsesquioxane.

\* \* \* \* \*